US008440008B2

(12) United States Patent  
Fronabarger et al.

(10) Patent No.: US 8,440,008 B2  
(45) Date of Patent: *May 14, 2013

(54) PREPARATION OF A LEAD-FREE PRIMARY EXPLOSIVE

(75) Inventors: John W. Fronabarger, Sun Lakes, AZ (US); Michael D. Williams, Gilbert, AZ (US)

(73) Assignee: Pacific Scientific Energetic Materials Company, Chandler, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/419,455

(22) Filed: Mar. 14, 2012

(65) Prior Publication Data

US 2012/0215004 A1  Aug. 23, 2012

Related U.S. Application Data

(63) Continuation of application No. 12/691,849, filed on Jan. 22, 2010, now Pat. No. 8,163,786, which is a continuation-in-part of application No. 11/676,846, filed on Feb. 20, 2007, now Pat. No. 7,833, 330.

(60) Provisional application No. 60/800,816, filed on May 16, 2006, provisional application No. 61/146,700, filed on Jan. 23, 2009.

(51) Int. Cl.
*C07D 257/04* (2006.01)
*H01B 1/16* (2006.01)

(52) U.S. Cl.
USPC .......................... 106/1.13; 514/381; 548/250

(58) Field of Classification Search .................. 106/1.13; 548/250
See application file for complete search history.

(56) References Cited

U.S. PATENT DOCUMENTS

| | | | |
|---|---|---|---|
| 2,066,954 A | 1/1937 | Von | |
| 2,480,141 A | 8/1949 | King | |
| 3,150,020 A | 9/1964 | Kilmer | |
| 3,351,015 A | 11/1967 | Wallack et al. | |
| 3,366,055 A | 1/1968 | Hollander, Jr. | |
| 3,486,453 A | 12/1969 | Billy | |
| 3,634,510 A | 1/1972 | Louis | |
| 3,791,301 A | 2/1974 | La Costa | |
| 4,093,623 A | 6/1978 | Gilligan et al. | |
| 4,094,879 A | 6/1978 | Bates et al. | |
| 4,133,707 A | 1/1979 | Andrew | |
| 5,039,812 A | 8/1991 | Norris | |
| 5,417,160 A | 5/1995 | Mei et al. | |
| 5,610,367 A | 3/1997 | Erickson et al. | |
| 5,639,986 A | 6/1997 | Evans | |
| 5,717,159 A | 2/1998 | Dixon et al. | |
| 5,831,208 A | 11/1998 | Erickdon | |
| 6,478,903 B1 | 11/2002 | John et al. | |
| 7,056,401 B2 | 6/2006 | Galluzzi | |
| 7,833,330 B2 * | 11/2010 | Fronabarger et al. | 106/1.13 |
| 8,062,443 B2 | 11/2011 | Fronabarger et al. | |
| 8,071,784 B2 * | 12/2011 | Fronabarger et al. | 548/250 |
| 8,163,786 B2 * | 4/2012 | Fronabarger et al. | 514/381 |
| 8,216,401 B1 | 7/2012 | Fronabarger et al. | |
| 8,298,324 B2 | 10/2012 | Fronabarger et al. | |
| 2002/0143189 A1 | 10/2002 | Sonti | |
| 2005/0183805 A1 | 8/2005 | Pile et al. | |
| 2006/0030715 A1 | 2/2006 | Hiskey et al. | |
| 2007/0161801 A1 | 7/2007 | Renz et al. | |
| 2009/0069566 A1 | 3/2009 | Fronabarger et al. | |
| 2009/0223401 A1 | 9/2009 | Fronabarger et al. | |
| 2010/0280254 A1 | 11/2010 | Fronabarger et al. | |
| 2011/0108172 A1 | 5/2011 | Fronabarger et al. | |
| 2012/0024178 A1 | 2/2012 | Fronabarger et al. | |
| 2012/0077983 A1 | 3/2012 | Fronabarger et al. | |
| 2012/0152140 A1 | 6/2012 | Fronabarger et al. | |

FOREIGN PATENT DOCUMENTS

| | | |
|---|---|---|
| EP | 0941180 | 9/1999 |
| GB | 1106277 | 3/1968 |
| JP | 2006115444 | 4/2006 |
| WO | WO9711926 | 4/1997 |
| WO | WO9902470 | 1/1999 |
| WO | WO9944968 | 9/1999 |
| WO | WO2008048351 | 4/2008 |
| WO | WO2009114347 | 9/2009 |
| WO | WO2010085583 | 7/2010 |

OTHER PUBLICATIONS

Office Action dated Apr. 2, 2009 in U.S. Appl. No. 11/676,846.
Office Action dated Jun. 2, 2009 in U.S. Appl. No. 11/676,846.
Office Action dated Jan. 5, 2010 in U.S. Appl. No. 11/676,846.
Response dated Apr. 20, 2009 in U.S. Appl. No. 11/676,846.
Response dated Sep. 2, 2009 in U.S. Appl. No. 11/676,846.
Response dated Mar. 8, 2010 in U.S. Appl. No. 11/676,846.
Request for Continued Examination dated Jul. 2, 2010 in U.S. Appl. No. 11/676,846.
Notice of Allowance dated Apr. 5, 2010 in U.S. Appl. No. 11/676,846.
Notice of Allowance dated Jul. 27, 2010 in U.S. Appl. No. 11/676,846.
Office Action dated Mar. 10, 2011 in related U.S. Appl. No. 12/900,531.
Response dated Jun. 10, 2011 in related U.S. Appl. No. 12/900,531.
Notice of Allowance dated Jul. 29, 2011 in related U.S. Appl. nNo. 12/900,531.
Office Action dated Jul. 19, 2011 in U.S. Appl. No. 12/691,849.
Response dated Aug. 19, 2011 in U.S. Appl. No. 12/691,849.
Office Action dated Sep. 20, 2011 in U.S. Appl. No. 12/691,849.
Response dated Dec. 16, 2011 in U.S. Appl. No. 12/691,849.
Notice of Allowance dated Feb. 8, 2012 in U.S. Appl. No. 12/691,849.
Office Action dated Feb. 14, 2012 in U.S. Appl. No. 13/252,547.
Response dated May 10, 2012 in U.S. Appl. No. 13/252,547.
Notice of Allowance dated Mar. 21, 2012 in U.S. Appl. No. 13/267,009.

(Continued)

*Primary Examiner* — Susannah Chung
(74) *Attorney, Agent, or Firm* — Dean W. Russell; Tiffany L. Williams; Kilpatrick Townsend & Stockton LLP

(57) ABSTRACT

Described are compounds and materials that may be used as a lead-free primary explosive, such as copper(I) nitrotetrazolate. Copper(I) nitrotetrazolate may he prepared by a process comprising the steps of: combining cupric salt, water and 5-nitrotetrazolate salt to form a mixture, heating the mixture, adding a reducing agent and stirring with continued heating. The method may also include combining cupric chloride, sodium 5-nitrotetrazolate and sodium ascorbate.

5 Claims, 2 Drawing Sheets

OTHER PUBLICATIONS

Office Action dated Jul. 23, 2010 in Australian Patent Application No. 2007313468.
Response dated Jun. 20, 2011 in Australian Patent Application No. 2007313468.
Office Action dated Jul. 28, 2010 in European Patent Application No. 07861248.8.
Response dated Oct. 5, 2010 in European Patent Application No. 07861248.8.
English Translation of Office Action dated Feb. 28, 2012 in Japanese Patent Application No. 2009-510942.
Barsan & Miller, . "Health Hazard Evaluation Report", HETA Report #91-0346-2572, FBI Academy, Quantico, Virginia, Apr. 1996, pp. ii-iv & 1-33.
Fronabarger, J. W. et al., "Preparation characterization and output testing of salts of 7-hydroxy-4,8-dinitrobenzofuroxan", Safe Journal Spring 2007 Survival and Flight Equipment Association (SAFE) US, XP008110604, Apr. 1, 2007, vol. 35, No. 1, pp. 14-18.
Hastie, J. W. et al., Molecular Basis for Secondary Flash Suppression, U.S. Army Research Office, Jul. 1, 1986, Document ARO 18375-CH, MIPR 102-84, 26 pages.
Patani, et al., "Bioisosterism: A Rational Approach in Drug Design", Chem. Rev., 1996. 96(8):3147-3176.
Spear, R. J. et al., "Structure and Properties of the Potassium Hydroxide-Dinitrobenzofuro Xan Adduct (KDNBF) and Related Explosive Salts", Propellants, Explosives, Pyrotechnics, No. XP008110603, Jun. 3, 1983, 8:85-88.
Talawar, et al., "Energetic co-ordination compounds : synthesis, characterization and thermolysis studies on bis-(5-nitro-2H-tetrazolato-$N^2$) tetraammine cobalt(III) perchlorate (BNCP) and its new transition metal (Ni/Cu/Zn) perchlorate analogues", Journal of Hazardous Materials, Elsevier Amsterdam, NL, XP022384449, ISSN : 0304-3894, Apr. 5, 2005, vol. 120, No. 1-3, pp. 25-35 (expecially p. 26).
Qualification and Final (Type) Qualification Procedures for Navy Explosives, Naval Sea Systems Command Instruction #8020.5C ("NAVSEAINST 8020.5C"), 40 pages (May 5, 2000).
Fourth Report on the Investigation of the Alternatives to Lead Azide and Lead Styphnate, NSWC-IH contract #N00174-06-C-0079, Sep. 20, 2007, pp. 1-23.
International Search Report and Written Opinion dated Apr. 12, 2010 in Application No. PCT/US2010/021695.
International Preliminary Report on Patentability dated Aug. 4, 2011 in Application No. PCT/US2010/021695.
International Search Report and Written Opinion in Application No. PCT/US07/04846.
International Search Report and Written Opinion dated Sep. 2, 2009 in Application Serial No. PCT/US2009/035952.
Notice of Allowance dated Jun. 28, 2012 in U.S. Appl. No. 13/282,547.
Office Action dated Oct. 8, 2012 in European Patent Application No. 10701427.6.
Restriction Requirement dated Dec. 21, 2012 in U.S. Appl. No. 13/194,147.
Office Action dated Jan. 2, 2013 in U.S. Appl. No. 13/612,901.
Response dated Jan. 16, 2013 in U.S. Appl. No. 13/194,147.
Office Action dated Feb. 27, 2013 in U.S. Appl. No. 13/194,147.
Response dated Apr. 1, 2013 in U.S. Appl. No. 13/612,901.

\* cited by examiner

PREPARATION OF A LEAD-FREE PRIMARY EXPLOSIVE

CROSS-REFERENCE TO RELATED APPLICATIONS

This application is a continuation of U.S. patent application Ser. No. 12/691,849entitled "Preparation of a Lead-Free Primary Explosive," filed Jan. 22, 2010, allowed, which is a continuation-in-part of U.S. patent application Ser. No. 11/676,846, entitled "Lead-Free Primary Explosive Composition and Method of Preparation," filed Feb. 20, 2007, now U.S. Pat. No. 7,833,330, which claims the benefit of U.S. Provisional Patent Application Ser. No. 60/800,816, entitled "Lead-Free Primary Explosive Composition and Method of Preparation," filed May 16, 2006, expired, and claims the benefit of U.S. Provisional Patent Application Ser. No. 61/146,700, entitled "Preparation of a Lead-Free Primary Explosive," filed Jan. 23, 2009, expired, the entire contents of each of which are incorporated herein by these references.

FIELD OF THE INVENTION

This invention relates to explosives, and in particular to preparation of a primary explosive that is free of lead.

BACKGROUND OF THE INVENTION

Explosive materials have a wide variety of applications. Primary explosives are sensitive explosive materials that are used, in relatively small quantities, to initiate a secondary or main explosive charge. Primary explosives should be sufficiently sensitive to be detonated reliably but not so sensitive as to be exceedingly dangerous to handle. Moreover, primary explosives should have sufficient thermal stability so as to not decompose on extended storage or temperature fluctuation. Many primary explosives in current use contain lead, with the most well-known example being lead azide. These lead-containing explosives are undesirable from an environmental standpoint, since their use and manufacture can contribute to or cause lead contamination.

Thus, there is a need in the art for lead-free explosive materials and in particular for lead-free primary explosives. Certain lead-free primary explosives have been proposed. For instance, nitrotetrazole-based primary explosives have been proposed in U.S. Pat. Nos. 4,093,623 and 4,094,879, as well as in U.S. Patent App. Pub. No. 2006/0030715. For a variety of reasons, some of these proposed compounds have failed to serve as commercially viable substitutes for lead-containing primary explosives, while others exhibit characteristics that make them undesirable for at least some commercial applications. For example, U.S. Patent App. Pub. No. 2006/0030715 discloses certain nitrotetrazole complexes (including copper(II) complexes) which form a crystalline structure that is difficult to work with from a handling and ordinance loading standpoint.

SUMMARY OF THE INVENTION

Embodiments of the invention are directed to a compound and material that may be used as a lead-free primary explosive, and methods for preparing such compound and material.

In one embodiment, a compound is prepared by the reaction of cupric chloride, sodium 5-nitrotetrazolate, sodium ascorbate, and water.

In another embodiment, a method of preparing a compound suitable as a primary explosive comprises the steps of: providing a cupric salt; providing a solvent; providing a 5-nitrotetrazolate salt; combining the cupric salt, solvent and 5-nitrotetrazolate salt to form a mixture; heating the mixture; adding a reducing agent; and heating the combination.

In some embodiments, a compound is prepared by providing cupric chloride; providing water; providing sodium 5-nitrotetrazolate; combining the cupric chloride, water, and sodium 5-nitrotetrazolate to form a mixture; heating the mixture; adding a solution of sodium ascorbate; and heating the combination.

DETAILED DESCRIPTION OF THE INVENTION

Figure 1:
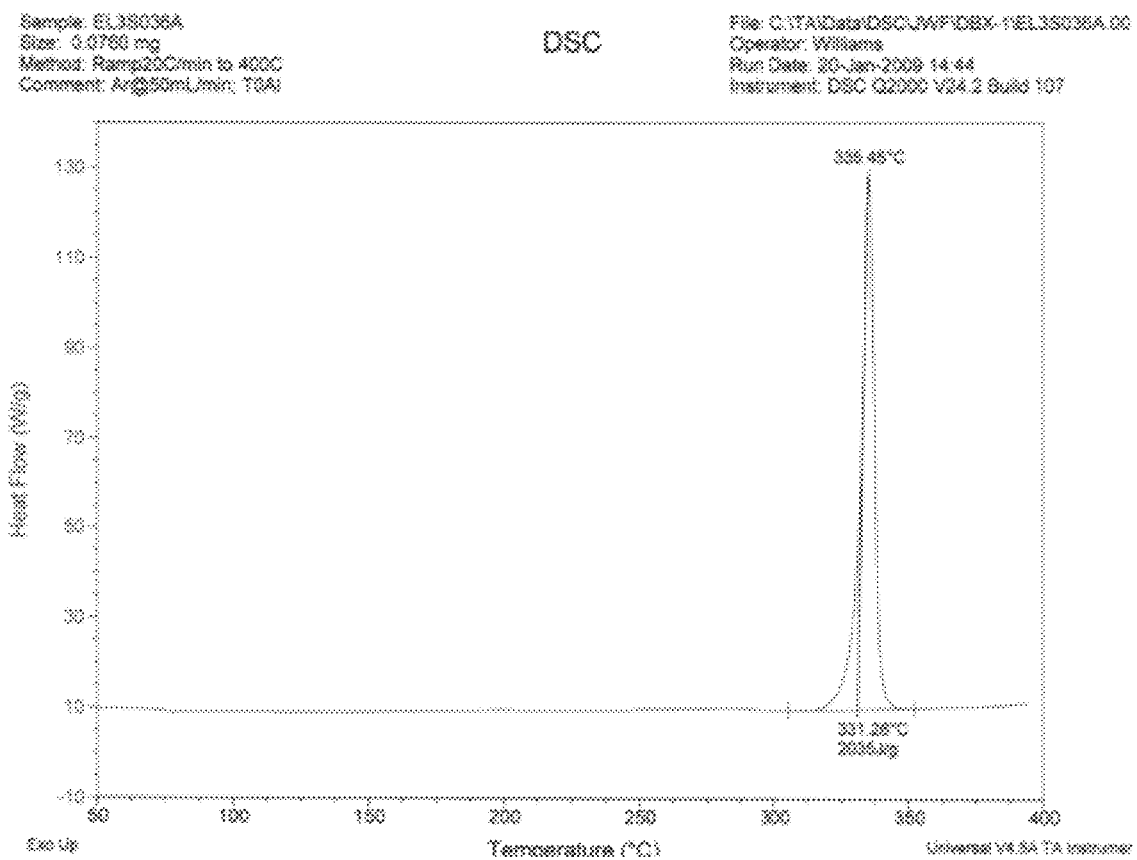
FIG. 1 shows the results of a differential scanning calorimetry (DSC) analysis on a material prepared according to the present techniques.

One aspect of the present subject matter is preparation of the compound copper(I) nitrotetrazolate. Also contemplated is any mixture which contains copper(I) nitrotetrazolate in a significant quantity (e.g. greater than about 1 weight percent, or alternatively, greater than about 5 weight percent).

Methods for preparing copper(I) nitrotetrazolate are contemplated in the present application. Copper(I) nitrotetrazolate may be prepared by reacting a copper(II) salt (for example, cupric chloride), a 5-nitrotetrazolate salt (for example, sodium 5-nitrotetrazolate) and a reducing agent (for example sodium ascorbate) in a solvent (for example, water). Any suitable copper(II) salt, or combination of copper(II) salts, may be employed. Suitable copper(II) salts include, but are not limited to, cupric chloride and cupric bromide. Likewise, any suitable 5-nitrotetrazolate salt, or combination of 5-nitrotetrazolate salts, may be employed. Suitable 5-nitrotetrazolate salts include, but are not limited to, sodium 5-nitrotetrazolate and potassium 5-nitrotetrazolate. Likewise, any suitable reducing agent, or combination of reducing agents, may be employed. Suitable reducing agents include, but are not limited to, sodium ascorbate and ascorbic acid. Likewise, any suitable solvent, or combination of solvents, may be employed. Suitable solvents include, but are not limited to, water, dimethyl sulfoxide (DMSO), as well as other polar organic solvents.

It will be understood that ionic versions of the salts referred to above may be employed in the preparation of copper(I) nitrotetrazolate. In other words, copper(I) nitrotetrazolate may be prepared by a reaction in which copper(I) ions and 5-nitrotetrazolate ions are combined to form copper(I) nitrotetrazolate.

The components may be reacted under conditions suitable to synthesize copper(I) nitrotetrazolate. Alternatively, the components may be reacted by mixing them together and then heating the mixture. The mixture may be heated in the temperature range of about 70° C. to about 150° C., alternatively in the temperature range of about 80° C. to about 130° C., alternatively to about 100° C. As yet another alternative, a reflux condenser may be employed, and the mixture may be heated to the reflux point. The duration of the heating or refluxing step may be a duration that is greater than about 1 minute, alternatively greater than about 35 minutes, alternatively from about 20 minutes to about 2 hours, alternatively from about 35 minutes to about 1 hour, alternatively about 50 minutes.

Regarding quantities of the components employed, 5-nitrotetrazolate may be supplied in a molar ratio of about 0.5 moles to about 2 moles 5-nitrotetrazolate per mole of copper (II). Alternatively, 5-nitrotetrazolate may be supplied in a molar ratio of about 0.8 moles to about 1.5 moles 5-nitrotetrazolate per mole of copper(II). Alternatively, 5-nitrotetrazolate may be supplied in a molar ratio of about 1 mole to about 1.2 moles 5-nitrotetrazolate per mole of copper(II). For example, sodium 5-nitrotetrazolate (NaNT) may be supplied in a molar ratio of about 0.5 moles to about 4 moles NaNT per mole of cupric chloride, alternatively about 0.8 moles to about 1.5 moles NaNT per mole of cupric chloride, alternatively about 1 mole to about 1.2 moles NaNT per mole of cupric chloride. Similarly, the reducing agent may be supplied in a molar ratio of about 0.5 mole to about 2 moles per mole of copper (II). Alternatively, the reducing agent may be supplied in a molar ratio of about 0.8 moles to about 1.5 moles per mole of copper (II). Alternatively, the reducing agent may be supplied in a molar ratio of about 1 mole to about 1.2 moles per mole of copper (II). For example, sodium ascorbate may be supplied in a molar ratio of about 0.5 moles to about 4 moles per mole of cupric chloride, alternatively about 0.8 moles to about 1.5 moles per mole of cupric chloride, alternatively about 1 mole to about 1.2 moles per mole of cupric chloride.

A solvent may be supplied in an amount that is suitable to effectuate the reaction between 5-nitrotetrazolate and formed copper(I). For example, water (or other solvent) may be supplied in an amount that is suitable to effectuate the reaction between a 5-nitrotetrazolate salt and a copper(I) salt. As a more specific example, water (or other solvent) may be supplied in an amount that is suitable to effectuate the reaction between NaNT and formed cuprous chloride.

The reaction components may be combined in any order or sequence suitable to effectuate the reaction. By way of non-limiting example, the reaction of 5-nitrotetrazolate salt and formed copper(I) salt may be carried out by adding an aqueous solution of 5-nitrotetrazolate salt to an aqueous suspension of copper(II) salt and adding a suitable reducing agent, or vice versa.

The copper(I) nitrotetrazolate formed by the reaction of cupric salt (for example, cupric chloride), a reducing agent (for example sodium ascorbate), water and 5-nitrotetrazolate salt (for example, sodium 5-nitrotetrazolate) may be a precipitate. The precipitate may be separated by a suitable method known to those of skill in the art. Alternatively, the precipitate may be separated by filtration. As yet another alternative, the precipitate may be separated using a flotation technique. It may be desirable to separate finer or lighter precipitate particles from coarser or heavier precipitate particles (for example, the coarser or heavier particles may be desirable from the standpoint of easy handling and loading). A flotation technique may be employed to achieve such a separation, as may other techniques known to those of skill in the art. Alternatively, the fine particles may be removed by careful decanting. Alternatively, the precipitate (which may, for example, be a dark brown precipitate) is collected over filter paper.

The precipitate formed by the reaction of cupric salt (for example, cupric chloride), a reducing agent (for example sodium ascorbate), water and 5-nitrotetrazolate salt (for example, sodium 5-nitrotetrazolate) may be washed. For example, the product may be washed either a single time or multiple times with water. Alternatively, the product may be washed either a single time or multiple times with alcohol, for example, isopropanol. Alternatively, the product may be washed in multiple steps and in any order with both water and alcohol. For example, the product may be washed sequentially with water and then isopropanol. The product may then be dried. For example, the product may be air dried. Alternatively the product may be dried in an oven at 65 to 80° C.

The present application also contemplates products made by the methods described above. In other words, the present application contemplates products made by reacting cupric salt (for example, cupric chloride), 5-nitrotetrazolate salt (for example, sodium 5-nitrotetrazolate), and a reducing agent (for example sodium ascorbate) in water, under the conditions and component quantities described above.

The products contemplated and made by the methods of the present application (in at least some aspects of the present subject matter, copper(I) nitrotetrazolate) are free of lead and have been found suitable for use as explosives and, in particular, as primary explosives. Thus, the present application also contemplates methods for preparing compounds suitable for use as primary explosives, and explosive devices employing such compounds. Benefits include low cost, ease of preparation and low toxicity waste streams and health benefits associated with low lead materials in both military and commercial applications.

The products contemplated and made by the methods of the present application (including copper(I) nitrotetrazolate) exhibit a crystalline structure that is suitable for loading and handling.

The foregoing is provided for purposes of illustrating, explaining, and describing embodiments of the present invention. Further modifications and adaptations to these embodiments will be apparent to those skilled in the art and may be made without departing from the scope or spirit of the invention.

EXAMPLES

The following examples demonstrate the preparation and characterization of a material as taught herein.

Example 1

Copper(I) nitrotetrazolate was prepared as follows. To 100 mL of a stirred hot (95-100° C.) aqueous solution of copper (II) chloride (0.79 g, 0.008 mol) and sodium 5-nitrotetrazolate dihydrate (1.70 g, 0.0096 mol) in a 250 mL beaker was added 8 mL of a 0.5 molar aqueous solution of sodium ascorbate at a rate of 1 mL/minute using a syringe pump. After the eight minute addition, the reaction mixture was boiled for an additional two minutes. The precipitate that was formed was collected on Whatman No. 1 filter paper, washed three times with water, twice with isopropanol, and then dried in a convection oven at 70° C. The yield of small red rust crystals was 1.218 g (85.7%).

Figure 2:
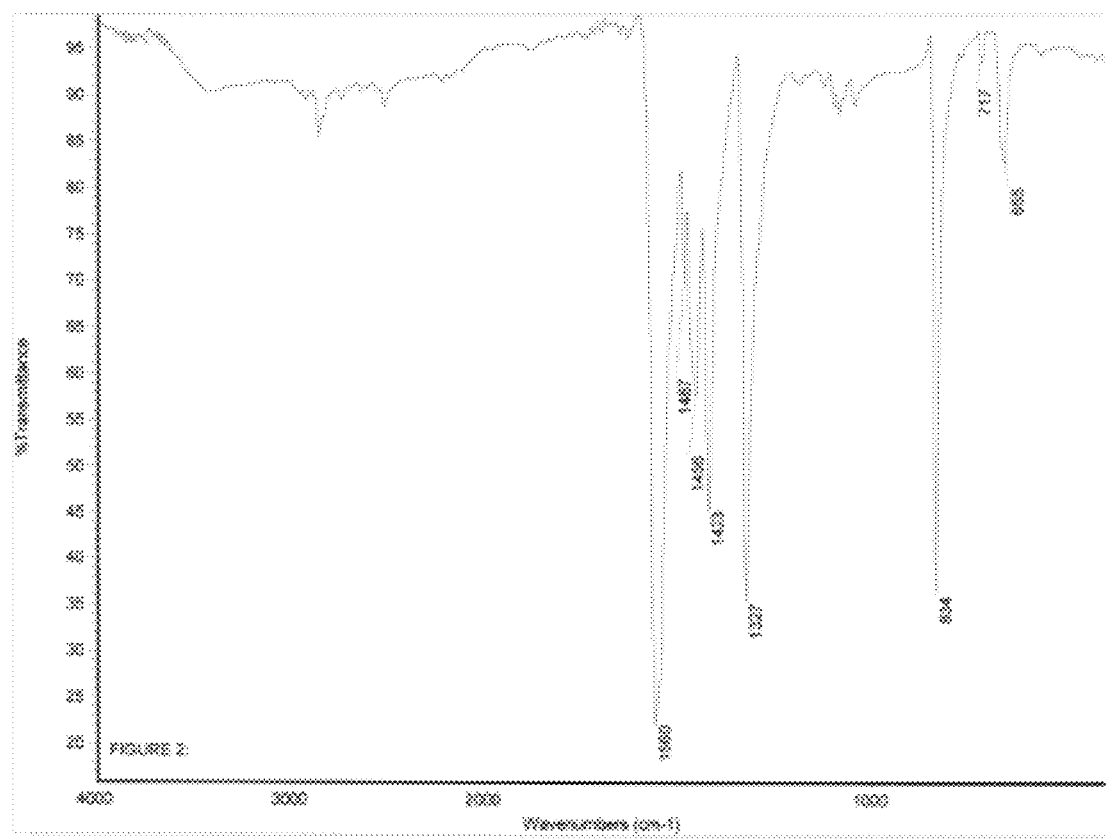
FIG. 2 shows the results of a Fourier Transform Infrared Spectroscopy (FTIR) analysis on a material prepared according to the present techniques.

The results of a differential scanning calorimetry (DSC) analysis on the solid are shown in FIG. 1. The results of a Fourier Transform Infrared Spectroscopy (FTIR) analysis on the solid are shown in FIG. 2.

Example 2

Copper(I) nitrotetrazolate was prepared as follows. To 100 mL of a stirred hot (95-100° C.) aqueous solution of copper (II) chloride (0.79 g) and sodium 5-nitrotetrazolate dehydrate (1.70 g) in a 250 mL beaker was added 8 mL of a 0.5 molar aqueous solution of ascorbic acid at a rate of 1 mL/minute using a syringe pump. After the eight minute addition, the reaction mixture was boiled for an additional two minutes. The precipitate that formed was collected on Whatman No. 1 filter paper, washed three times with water, twice with isopropanol, and then dried in a convection oven at 70° C.

While the present subject matter has been described and illustrated by reference to particular embodiments, it will be appreciated by those of ordinary skill in the art that the subject matter lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

What is claimed is:

1. Copper(I) nitrotetrazolate, wherein copper(I) has one valence electron, prepared by a process comprising the steps of:
   (a) combining cupric chloride, water, and sodium 5-nitrotetrazolate to form a mixture;
   (b) heating the mixture;
   (c) adding a solution of sodium ascorbate to the mixture; and
   (d) heating the solution of sodium ascorbate and the mixture.

2. The copper(I) nitrotetrazolate of claim 1 characterized by a Differential Scanning Calorimetry curve with a distinguishing peak at about 335 degrees C.

3. The copper(I) nitrotetrazolate of claim 1 characterized by a Differential Scanning Calorimetry curve substantially as shown in FIG. 1.

4. The copper(I) nitrotetrazolate of claim 1 characterized by a Fourier Transform Infrared Spectroscopy spectra with distinguishing peaks at about 1560, 1487, 1456, 1423, and 1327.

5. The copper(I) nitrotetrazolate of claim 1 characterized by a Fourier Transform Infrared Spectroscopy spectra as shown in FIG. 2.

* * * * *